United States Patent [19]

Angell

[11] Patent Number: 4,709,696

[45] Date of Patent: Dec. 1, 1987

[54] SIGHT CORRECTION ATTACHMENT FOR RESPIRATORS

[75] Inventor: Cyril N. E. Angell, Trowbridge, England

[73] Assignee: Avon Industrial Polymers Limited, Melksham, England

[21] Appl. No.: 806,463

[22] Filed: Dec. 9, 1985

[30] Foreign Application Priority Data

Dec. 14, 1984 [GB] United Kingdom ................ 8431592

[51] Int. Cl.[4] .......................... A62B 10/08; A61F 9/02

[52] U.S. Cl. .................................. 128/201.12; 2/441; 351/86

[58] Field of Search ...................... 128/201.12, 200.24; 2/427, 441, 426, 442, 443, 444; 350/410, 248, 252, 254, 582; 351/47, 57–59, 62, 83, 86; D2/157, 178, 234; D16/116, 128, 129

[56] References Cited

U.S. PATENT DOCUMENTS

| | | | |
|---|---|---|---|
| 1,923,567 | 8/1933 | Baker | 351/57 |
| 2,427,918 | 9/1947 | Malcom et al. | 2/441 |
| 2,846,684 | 8/1958 | Hill | 2/441 |
| 3,552,840 | 1/1971 | Braget | 351/154 |
| 4,056,853 | 11/1977 | Bohazzini et al. | 351/86 |
| 4,338,009 | 7/1982 | Vosper | 351/86 |

FOREIGN PATENT DOCUMENTS

| | | | |
|---|---|---|---|
| 0106447 | 4/1984 | European Pat. Off. | 128/201.12 |
| 642450 | 3/1937 | Fed. Rep. of Germany | 128/201.12 |
| 49815 | 5/1939 | France | 128/201.12 |
| 1282140 | 12/1961 | France | 128/201.12 |
| 506821 | 8/1937 | United Kingdom | 128/201.12 |
| 530683 | 12/1940 | United Kingdom | 2/441 |

*Primary Examiner*—William E. Kamm
*Assistant Examiner*—Karin M. Reichle
*Attorney, Agent, or Firm*—William R. Hinds

[57] ABSTRACT

A sight-corrective lens is attached between an eyepiece of a respirator and the eye of the wearer by a monocular mount into which the lens fits as if into a standard spectacle frame. Attachment devices for the mount are apertured lugs on a surround of the eyepiece and tabs on the mount. By making the tab and mount in one position of different tangential width from the tab and mount in the other, a desired unique positioning of the lens is assured. The mount may have a seal ring of which the deformable ridge is pretensioned against the eyepiece by the fitting of the tabs in the lugs to prevent ingress of moisture or particles between them.

8 Claims, 7 Drawing Figures

SIGHT CORRECTION ATTACHMENT FOR RESPIRATORS

FIELD OF THE INVENTION

This invention relates to means for attachment of sight-correcting lenses to a respirator.

BACKGROUND OF THE INVENTION

The problem of correcting for sight defects of the wearer of a respirator is a well known one.

Previous attempts to solve it have concentrated either on providing that the eyepiece of the respirator itself shall be a sight-corrective lens (e.g. CH-A-365948) or that a separate sight-corrective lens shall be added on to the outside of the respirator eyepiece (e.g. U.S. Pat. No. 2,737,659).

The first has the clear disadvantage of the need for customized preparation of complete respirator eyepieces, desirable materials for which, moreover, will not necessarily have the most suitable properties for sight-corrective lenses; the second mainly that the sight-corrective lens will be further away from the eye than would normally be desired, but also that the sight-corrective lens is accessible to damage or dislodgement.

In U.S. Pat. No. Des. 237,757 an eyepiece of a goggle has projecting tabs, presumably for securing it to the straps etc which hold the goggle to the head of the user.

SUMMARY OF THE INVENTION

The present invention is concerned to avoid both of these disadvantages by allowing a sight-corrective lens to be mounted on the inner side of the eyepiece of a respirator i.e. between it and the wearer's eye. These lenses may be individual monocles. Furthermore the means of attachment inside the respirator may be "handed" that is to say may be such that a lens for the right eye can only be attached behind the right hand eyepiece, and for the left hand similarly. This may be by the asymmetric provision of attachment means on the eypiece surround, with coupling means on the mount of a sight-corrective lens which can be fixed uniquely to the attachment means.

In a particular embodiment of the invention we modify the surround of an eyepiece as seen for example in FIG. 2 of our co-pending published European application EP-A-0106447 or in Dodd U.S. Pat. No. 4,449,255 (EP-A-035849) the disclosures of which are hereby incorporated by reference, by the addition on the inner side of that surround of apertured lugs one at each lateral side of the eyepiece, and we provide a mount for a sight-corrective lens which has tabs for insertion through the apertures of the lugs. To provided "handedness" the apertures in the respective lugs may be of different extent, with the tabs differing correspondingly, so that the mount as a whole can only be fixed in one attitude in relation to the facepiece. Two such mounts are provided for the respective eyes of the wearer; the mounts may be identical (except for their handedness if provided) so that any one of a plurality of standard prescription lenses may be fitted into them exactly as if they were the standard frame of a pair of spectacles. They are however preferably separate monocles secured individually to the surrounds of the eyepieces of the respirator thereby avoiding the need for any link going across the bridge of the nose of the wearer or for any arms going back to his ears as in a conventional spectacle frame.

In a modification, the mount may be provided with seal means to engage the eyepiece of the respirator, and the attachment means be arranged to bias the seal means into contact with the eyepiece.

DESCRIPTION OF THE DRAWINGS

A particular embodiment of the invention will now be described by reference to the accompanying drawings wherein.

DESCRIPTION OF A PARTICULAR EMBODIMENT

Figure 1:
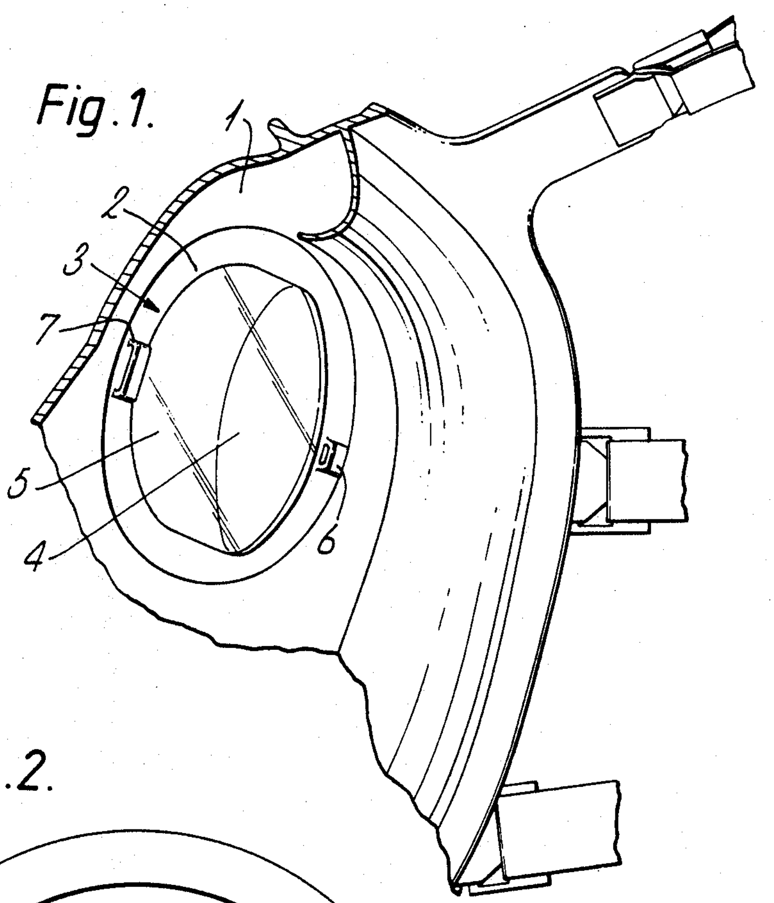
FIG. 1 is a partial median section of a respirator facepiece showing an eyepiece

FIG. 1 shows the facepiece 1 of a respirator which has been sectioned so that in the upper half of the facepiece we can look into its right hand side. A circular surround 2 is formed in the rubber material of the facepiece into which is fitted an eyepiece 3. The surround and eyepiece are preferably as described in our said co-pending application the eyepiece 3 having a configuration whereby a concave-convex portion 4 of which the radii of curvature on both sides are equal and which therefore has no optical corrective effect, is presented at an advantageous angle to the eye by the provision of an angled, crescent-like wall 5 linking it to a planar rim of the eyepiece which is held in the surround.

As compared to the said application however the present surround is modified by the provision of attachment means 6,7 whereby a mount containing a monocular sight-corrective lens may be attached inside the eyepiece, between it and the eye of the wearer.

Figure 2:
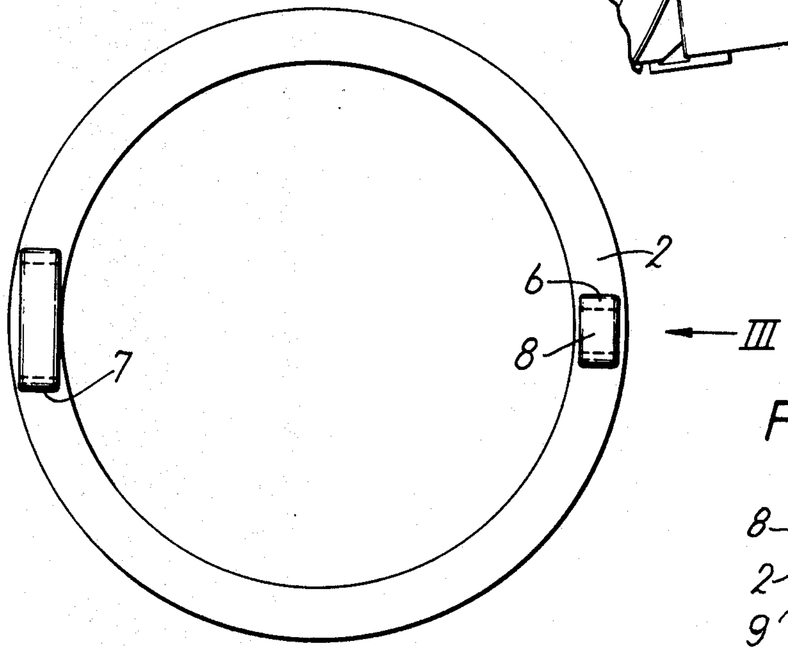
FIG. 2 is a face view of a rim for an eyepiece in that facepiece
Figure 3:
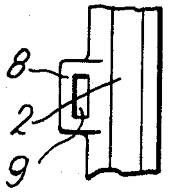
FIG. 3 is a view on the arrow III of FIG. 2

FIGS. 2 and 3 are a face and side view of the surround 2. The attachment means 6,7 are mounted diametrically opposed to each other across the circular surround 2 but are asymmetric. Attachment means 6 are seen in detail in FIG. 3. It is a comparatively wide lug the arch 8 of which bridges an aperture 9 which penetrates radially of the surround 2. The attachment means 7 is exactly the same except that the arch of its aperture is wider i.e. the aperture is of greater tangential extent.

Figure 4:
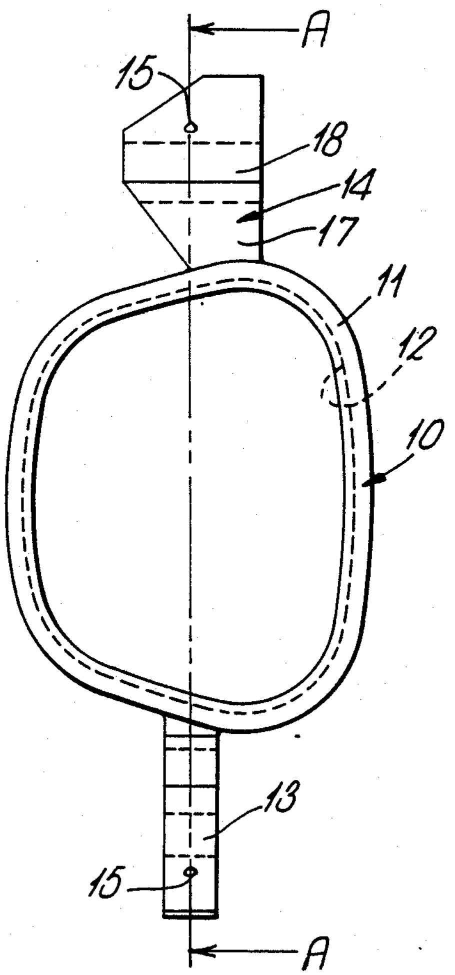
FIG. 4 is a face view of one monocle mount for securing a lens inside the eyepiece of the respirator
Figure 5:
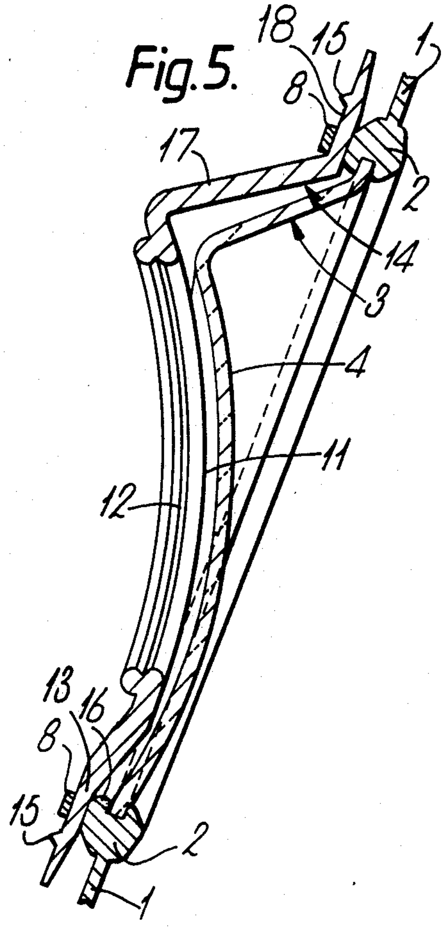
FIG. 5 is a section analogous to the plane AA of FIG. 4 of part of the respirator with the mount in position.

The mount 10 by which an optical lens may be secured inside the eyepiece of the respirator is seen in FIGS. 4 and 5.

Looking first at FIG. 4, the mount 10 is a one-piece moulding of a suitable thermoplastic or thermosetting material for example EPDM or EPT. The frame part 11 of the mount is of a standard shape for receiving a prescription sight-corrective lense 19 the edge of which fit into a continuous groove 12 around the aperture of the frame in just the same manner as into a normal spectacle frame. Opposed across the frame are tabs 13,14. The end portion of the tab 13 is laterally dimensioned so that it fits snugly within the tangential extent of the aperture 9 of the attachment means 6. It has a pip 15 on one surface. The distance along the tab between that pip and a shoulder 16 (FIG. 5) on the other face of the tab 13 is slightly greater than the radial extent of the arch 8. Therefore if the tab is pushed through the aperture 9 until the pip 15 emerges at the other side of the arch, the tab and thereby the mount will be positioned and retained by the attachment means 6 disposed between the shoulder and the pip.

The tab 14 includes a portion 17 which is at an angle to the general plane of the frame 11 so as to accommodate the shape of the respirator eyepiece used, such as eyepiece 3. In this embodiment the portion 17 fits along the crescent angled wall part 5 of the eyepiece. At its end it has a tab end portion 18 generally coplanar with the tab end portion 13 and like that tab end portion provided with a locating pip 15. It can be seen from FIG. 4 that the width of the tab 14 between the portion 17 and the pip 15 is considerably greater than the width of the tab 13 and in fact is suitable to fit snugly within the aperture in the attachment means 7. Also the spacing between the pip 15 and portion 17 is such as to provide a securely positioned coupling to that attachment means. Because of the different tangential extent of the apertures of the attachment means 6 and 7 and because of the different widths of the tab parts 18,13 the mount can only be assembled within the eyepiece in one orientation, that is to say a lens intended for the wearer's right eye cannot be fitted to the inside of the left eyepiece of the face piece of the respirator, where of course the disposition of the wide and the narrow attachment means will be the mirror image of that described, in relation to the median plane of the respirator facepiece.

Figure 6:
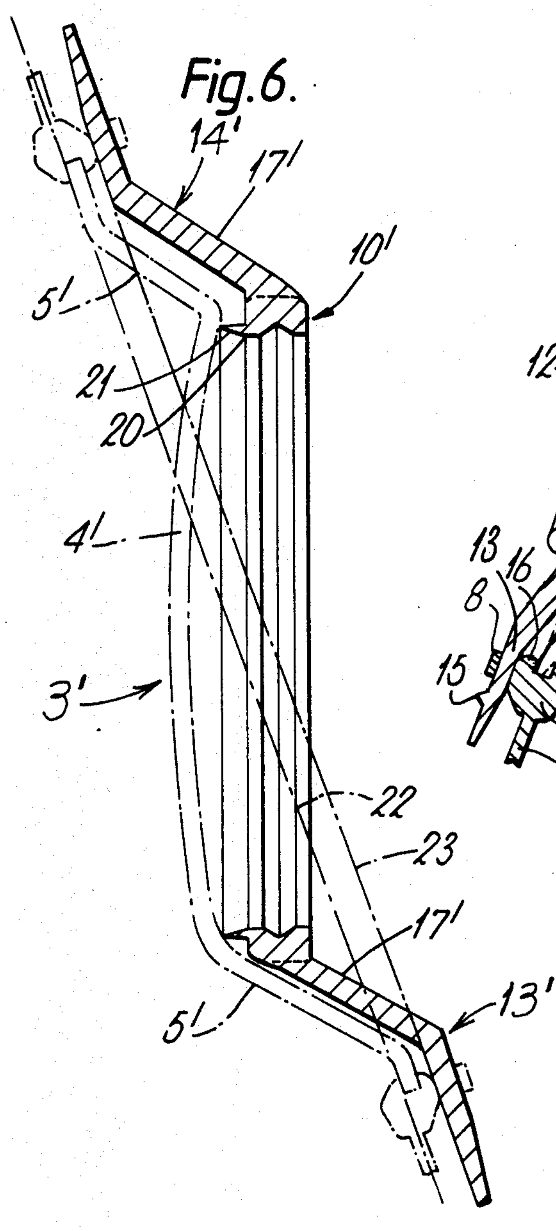
FIG. 6 shows a modification, in section analogous to the plane AA.
Figure 7:
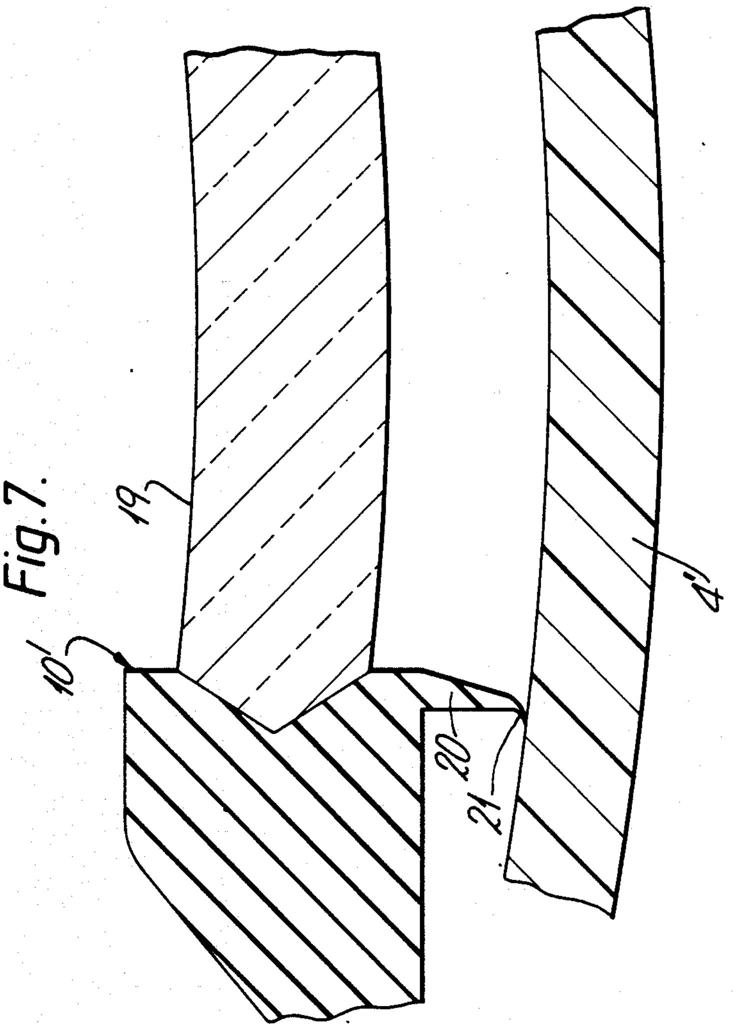
FIG. 7 is a detail of FIG. 5.

In a modification, seen in FIGS. 6 and 7, a mount 10′ which is similar to mount 10 has a seal ring 20 continuously around the frame, on the face which will be nearer the respirator eyepiece. The ring is of tapered section so that its extremity 21 is comparatively deformable. This extremity is, in use, pressed against the inner surface of the respirator eyepiece portion 4′. This pressing is due to the dimensioning of the ring 20 and of the attachment means so that when the latter are engaged there is stressing of the tabs 13′, 14′ in the sense to press the seal toward and against the inner surface of eyepiece 4′. Essentially, this simply means that the dimensions, configurations and orientations are such that when the tabs 13′, 14′ are inserted into the apertured lugs, the seal is pressed against the eyepiece. The seal ring prevents access of particles or moisture to the mutually adjacent faces of the lens in the mount and of the eyepiece. FIG. 6 shows how the mount may have two angled portions 17′ one on each tab, to accommodate to a type of eyepiece 3′ where the concave-convex (or planar) portion 4′ is not set to one side of but intercepts the plane 22 of its rim, with crescent walls 5′ on both sides of the section. The plane 23 of the tabs of the mount is of course parallel to plane 22.

It can be seen that this is an extremely elegant design of a monocle mount and mounting system, especially in the one piece nature which can be achieved in the mount and in the fact that no special tools or techniques are required for the assembly of the mount to the respirator eyepiece. At least where thermosetting materials are used for the mount material, lenses can readily be exchanged in a given mount. Alternatively, of course, different monocles may be supplied for a given user for use with one respirator e.g. for different intended activities.

Of course the principle enunciated for the ready attachment of sight corrective lenses inside the eyepiece of a respirator is not restricted to use with the eyepiece and surround design which has been described as preferred; the lenses may using the present system be equally well mounted behind purely planar eyepieces for example.

We claim:

1. A mount means for receiving a sight corrective lens and attaching the sight corrective lens adjacent an eyepiece of a respirator having projecting apertured lugs of different widths, the mount means having projecting tabs of different widths, the tabs being for respectively engaging the apertures of the lugs whereby to maintain the lens in said mount means adjacent to the eyepiece in a unique orientation relative thereto.

2. A mount as claimed in claim 1 wherein said tabs bear detent means for maintaining a preferred position of engagement between the tabs and lugs, respectively.

3. A mount as claimed in claim 1 wherein said mount means includes a continuous lip seal adapted for engagement with the eyepiece so as to seal the area between the eyepiece and the lens.

4. A mount as claimed in claim 3 wherein the engagement of said lip seal is under stress due to engagement between the lugs and mount means.

5. A mount as claimed in claim 1 wherein said mount means includes a lens frame, the tabs have outer portions which are generally coplanar, said frame being generally at an angle to said plane, and at least one tab has an angle portion joining the outer portion to the lens frame of the mount means.

6. In a respirator having an interior and an exterior and having an eyepiece adapted to be positioned in front of the eye of a wearer of the respirator and a sight-corrective lens adapted to be positioned between the eyepiece and the eye, the improvement comprising a mount means for mounting the sight-corrective lens having outwardly projecting tabs of respectively unequal widths, and a mount means for mounting the eyepiece having lugs projecting toward the interior and away from the exterior and hence toward the eye of the wearer, and apertures in said lugs for receiving said tabs, said apertures being of unequal width correlated to the unequal widths of the tabs such that a unique orientation of the lens is determined by engagement of the tabs in the apertures.

7. The improvement as claimed in claim 6 further comprising a seal ring on said lens mount means for forming a lip seal against the eyepiece, said engagement of said lugs and said tabs being adapted to urge said seal ring against said eyepiece.

8. A mount means for receiving a sight-corrective lens and attaching the sight-corrective lens adjacent an eyepiece of a respirator having projecting apertured lugs, the mount means having projecting tabs for respectively engaging the apertures of the lugs whereby to maintain a lens in said mount means adjacent to the eyepiece, and a seal ring on said mount means for surrounding said lens and adapted to face the eyepiece, the engagement of the tabs and lugs and the dimensions of the seal ring being such as to press the seal ring into engagement with the eyepiece when the tabs and apertures are engaged so as to seal the space encompassed by the seal ring, the lens and the eyepiece.

* * * * *